United States Patent [19]

Vijil-Rosales

[11] 4,372,293
[45] Feb. 8, 1983

[54] APPARATUS AND METHOD FOR SURGICAL CORRECTION OF PTOTIC BREASTS

[76] Inventor: Cesar A. Vijil-Rosales, 5642 Indigo, Houston, Tex. 77096

[21] Appl. No.: 219,670

[22] Filed: Dec. 24, 1980

[51] Int. Cl.³ .............................................. A61B 19/00
[52] U.S. Cl. ................................. 128/1 R; 128/335.5; 3/36
[58] Field of Search ............ 128/335.5, 334, DIG. 14, 128/1; 3/36

[56] References Cited

U.S. PATENT DOCUMENTS

| | | | |
|---|---|---|---|
| 3,054,406 | 9/1962 | Usher | 128/334 |
| 3,124,136 | 3/1964 | Usher | 128/334 |
| 3,293,663 | 12/1966 | Cronin | 3/36 |
| 3,665,520 | 5/1972 | Perras et al. | 3/36 |
| 4,034,763 | 7/1977 | Frazier | 128/335.5 |

OTHER PUBLICATIONS

Surgery, Gynecology & Obstetrics, vol. 131, pp. 525-530, Sep., 1970.
The American Journal of Surgery, vol. 138, pp. 740-741, Nov., 1979.
Plastic Surgery, By Drs. William C. Grabb and James W. Smith, pp. 750-757, (Dec., 1979).

Primary Examiner—Stephen C. Pellegrino
Attorney, Agent, or Firm—Fulbright & Jaworski

[57] ABSTRACT

An apparatus for the surgical correction of ptosis of the breast and a method of surgery implementing such an apparatus. A ribbon of inert mesh is connected between the mammary gland and the clavicle, or other element of the skeletal structure above the breast, so as to give support to the breast. The ribbon of mesh may be constructed with a trocar point needle or a cutting edge needle on one end for implementing surgical attachment to the mammary. On the opposite end of the mesh ribbon may be attached a blunt rod to conduct the ribbon beneath the skin from the mammary to the point of attachment on the skeletal structure.

10 Claims, 2 Drawing Figures

APPARATUS AND METHOD FOR SURGICAL CORRECTION OF PTOTIC BREASTS

BACKGROUND OF THE INVENTION

1. Field of the Invention

The invention relates generally to the medical field commonly known as plastic, cosmetic, or reconstructive surgery. The present invention relates more particularly to an improved method of surgically correcting ptosis of the breast and other defects of the mammaries and to a device which is implemented in that method.

2. Description of Prior Art

Ptosis is a condition of a body organ in which the organ sags or falls. Mastopexy is the term used to describe the surgical correction of mammary ptosis when no volume alteration is indicated. Some forms of mastopexy, however are incorporated with augmentation mammoplasty. Descriptions of several modes of surgical correction of ptosis of the breast are given in PLASTIC SURGERY, by Drs. William C. Grabb and James W. Smith, at pages 750-757 (December, 1979). Included is a method, depicted as the "Technique of Dufourmental and Mouly" in which an "inferiorly based dermoglandular flap of lateral breast tissue is rotated superiorly and medially into a retromammary pocket," with the rotated flap being affixed to the periosterum of the third rib. See PLASTIC SURGERY, at page 752. Another technique, described at pages 753-755 includes the steps of making a circumareolar incision, undermining of the circumareolar skin, separation of the gland from the pectoral fascia, and rotation of the axiallary tail into the retromammary space and suturing to the posterior aspect of the gland.

SUMMARY OF THE INVENTION

The present invention is directed to a surgical method of correction of ptosis of the breast and other defects of the mammaries. The invention is also directed to an apparatus implemented in that method.

A physiologically inert mesh formed into an elongated ribbon-like shape is attached at its lower end to the mammary gland and at its upper end to the clavicle or other element of the skeletal structure or the fascia above the breast. The mesh is situated beneath the skin, preferably being conducted through a layer of subcutaneous tissue.

The mesh material is selected so that it has sufficient tensile strength and inelasticity to withstand stretching, thereby insuring that the breast remains in its intended position after surgery. Furthermore, a mesh material may be selected to allow the body tissue to grow into and become interwoven with the mesh.

The mesh may be attached at its lower end to a trocar point needle or to a cutting edge needle useful in passing the ribbon through the breast tissue. These elements are useful because their cutting edges aid in the surgical connection of the mesh to the relatively tough breast tissue. Additionally, a blunt rod may be attached to the opposite end of the mesh to aid in conducting the mesh through the body tissue from the breast to the point of attachment on the skeletal structure. Alternatively, blunt rods may be attached to both ends of the mesh to aid in passing the mesh under the inferior border of the mammary gland.

The number and location of the mesh connectors may be varied according to the particular defect and geometry of the patient. This procedure would, however, subject the patient to surgery normally having a relatively short duration and involving minimal trauma.

It is, therefore, an object of this invention to provide a device useful in corrective surgery of ptosis of the breast and other defects of the breast.

Another object of the present invention is to provide a mammary suspension kit including an element to assist in conducting the suspension element beneath the skin between the points of attachment.

Yet another object of the present invention is to provide a mammary suspension kit including an element to assist in passing the suspension element through or under the breast tissue.

Yet another object of the present invention is to provide an apparatus for correcting ptosis of the breast, which apparatus will become enmeshed with the tissue of the subject patient.

A further object of the present invention is to provide a surgical method for correcting ptosis of the breast and other defects of the mammaries.

A still further object of the present invention is to provide a surgical method for correcting ptosis of the breasts and other defects of the mammaries involving a procedure of short duration in which the patient experiences minimal trauma.

Other and further objects, features, and advantages will be apparent from the following description of the presently preferred embodiments of the invention, given for the purpose of disclosure, when taken in conjunction with the accompanying drawing.

BRIEF DESCRIPTION OF THE DRAWINGS

The invention will be more readily understood from a reading of the following specifications and by reference to the accompanying drawings, forming a part thereof, wherein examples of embodiments of the invention are shown, and wherein.

DESCRIPTION OF THE PREFERRED EMBODIMENTS

Figure 1:
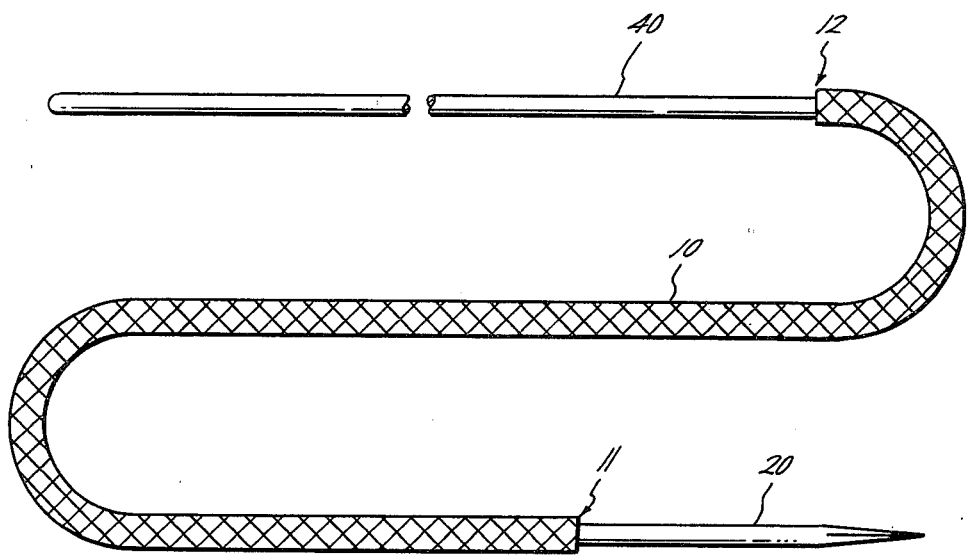
FIG. 1 is a lateral view of an embodiment of the apparatus of this invention which includes the ribbon of mesh, a trocar point needle, and a blunt end stainless steel rod.

By way of illustration and not limitation, this detailed description presents preferred embodiments of my invention. It will be readily apparent to one skilled in this art that my invention can be incorporated into other devices and methods in manners similar to the ways in which the device and method are herein illustrated without departing from the scope of my invention.

"Ptosis of the breast" generally describes that condition existing when the mammary has fallen below that level which is deemed aesthetically desirable. This condition is more likely to occur in older patients or in those having relatively large breasts, but it is also found in both the young and in women having smaller breasts. Under the present invention, a suspension device, fashioned in the form of a harness, is surgically implanted in the patient so as to provide corrective suspension of the defective breast.

Referring to the drawing, the reference numeral 10 generally designates the physiologically inert mesh utilized in implementing the procedure described herein. The mesh is formed into an elongated ribbon-like shape and is sufficiently long to extend between its points of connection on the mammary and the skeletal structure. The material chosen for this mesh 10 preferably has sufficient tensile strength and inelasticity that the mesh 10 may reasonably be expected to perform its function throughout the patient's life without necessitating replacement, and without stretching and thereby decreasing its efficiency as a suspension device.

Material appropriate for the mesh 10 may be selected from a number of materials, including both monofilaments and multifilaments. Such materials include, but are not limited to, polypropylene, dacron, teflon, and polyethylene.

Figure 2:
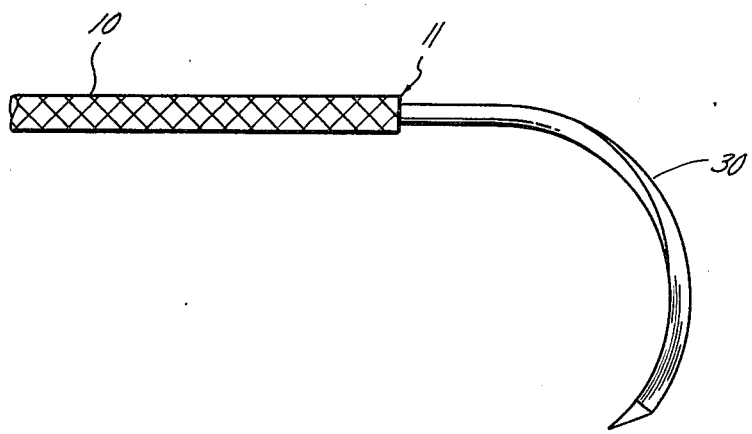
FIG. 2 is a lateral view of another embodiment of the apparatus of this invention which includes the ribbon of mesh and a cutting edge needle.

The mesh 10 is surgically attached at its lower end 11 to the mammary gland at a point or points to be determined according to the size and geometry of the subject breast. In fact, a plurality of strands of mesh 10 may be required with some patients. The attachment to the mammary may be accomplished via conventional suturing between the mesh 10 and the gland. In the embodiment illustrated in FIG. 1, attachment may be accomplished with the aid of the trocar point needle 20 attached to lower end 11 of mesh 10. In the alternative embodiment illustrated in FIG. 2, cutting edge needle 30, similarly attached to mesh 10, is provided for use in the attachment process. Once the needle 20 or 30 has served its purpose in facilitating the connection of lower end 11 to the gland, it is removed from the mesh 10. In order to induce the suspension of the ptotic breast, the mesh must at this point be connected to a fixed point above the breast. Various elements of the skeletal structure or the fascia are available as suitable bases for attachment. In particular, the clavicle above the defective breast is an appropriate point of attachment.

Attachment to the clavicle is made by incision through the skin in that area. After attachment of the mesh 10 to the mammary, the mesh 10 may be routed beneath the skin to the specific selected point on the clavicle at which attachment of the mesh 10 is made. A preferred method includes the conduction of upper end 12 of mesh 10 from the mammary through the subcutaneous tissue to the clavicle. In the embodiment illustrated in FIG. 1, a blunt rod 40 of stainless steel is provided at upper end 12 to assist in the conduction of mesh 10. Using the aforementioned incision in the area of the clavicle, upper end 12 is then connected to the clavicle by conventional surgical techniques. Before completion of the connection however, the length of mesh 10 is adjusted to provide the appropriate suspension force on the breast. Where a plurality of strands of mesh 10 are utilized, the skeletal connections may be fastened at a single area of the skeletal element selected, or, if the requirements of the patient dictate, the connection may be fastened at a plurality of points.

An alternative corrective procedure includes the location of the mesh, in the fashion of a sling, under the inferior border of the mammary gland, with both ends of the mesh attached to the skeletal structure or fascia above the mammary.

After the described method is implemented, the tissue growth of the patient in the area of the mesh connector will interweave with the mesh 10. As in the hernia surgery where such mesh is currently utilized, this interweaving of tissue and mesh will serve to increase the strength of the connector and enhance its effectiveness as a suspension device. Furthermore, the use of the described apparatus and the method of this invention will normally subject the patient to less trauma and require both a procedure and a recovery period of shorter duration than that which occurs in the current methods, such as those where resection of the breast is involved.

The foregoing disclosure and description of the invention is illustrative and explanatory thereof, and various changes in the size, shape, and materials, as well as details of the illustrated construction, and of the procedure described herein, may be made within the scope of the appended claims and without departing from the spirit of the invention.

What is claimed is:

1. A method of repairing ptosis of the breast and other defects of a mammary gland, comprising:
   attaching the lower end of a ribbon of physiologically inert mesh to the tissue of the mammary gland;
   conducting the ribbon beneath the surface of the skin upward to a predetermined area of the fascia or the skeletal structure above the mammary, and;
   attaching the upper end of the ribbon to the skeletal structure or the fasica above the mammary, the ribbon being sufficiently taut to impede the fall of the breast below a predetermined position.

2. The method of claim 1, wherein the conduction of the ribbon beneath the surface of the skin is accomplished by attaching the upper end of the ribbon to a blunt rod and directing the rod and ribbon to the predetermined area of the fascia or skeletal structure.

3. A method of repairing ptosis of the breast and other defects of a mammary gland, comprising:
   attaching the lower end of a ribbon of physiologically inert mesh to the breast, with a trocar point needle attached to the lower end of the ribbon and serving to pass the ribbon through the breast tissue;
   removing said trocar point needle from the attached ribbon;
   conducting the ribbon beneath the surface of the skin upward to a predetermined area of the skeletal structure or fascia above the mammary, and;
   attaching the upper end of the ribbon to the skeletal structure or fascia above the mammary, the ribbon being sufficiently taut to impede the fall of the breast below predetermined position.

4. The method of claim 3, wherein the conduction of the ribbon beneath the surface of the skin is accomplished by attaching the upper end of the ribbon to a blunt rod and directing the rod and ribbon to the predetermined area of the fascia or skeletal structure.

5. A method of repairing ptosis of the breast and other defects of a mammary gland, mammaries, comprising:
   attaching the lower end of a ribbon of physiologically inert mesh to the breast, with a cutting edge needle attached to the lower end of the ribbon and serving to pass the ribbon through the breast tissue;
   removing said cutting edge needle from the attached ribbon;
   conducting the ribbon beneath the surface of the skin upward to a predetermined area of the skeletal structure or fascia above the mammary, and;
   attaching the upper end of the ribbon to the skeletal structure or fascia above the mammary, the ribbon being sufficiently taut to impede the fall of the breast below a predetermined position.

6. The method of claim 5, wherein the conduction of the ribbon beneath the surface of the skin is accomplished by attaching the upper end of the ribbon to a blunt rod and directing the rod and ribbon to the predetermined area of the fascia or skeletal structure.

7. A method of repairing ptosis of the breast and other defects of a mammary gland, comprising:
attaching the lower end of a ribbon of physiologically inert mesh to the tissue of the mammary gland;
conducting the ribbon beneath the surface of the skin upward to a predetermined area of the skeletal structure or fascia above the mammary by leading the ribbon through the desired path by means of a directing means attached to the upper end of the ribbon;
removing said directing means from the attached ribbon, and;
attaching the upper end of the ribbon to the skeletal structure or fascia above the mammary, the ribbon being sufficiently taut to impede the fall of the breast below a predetermined position.

8. The method of claim 7, wherein the conduction of the ribbon beneath the surface of the skin is accomplished by attaching the upper end of the ribbon to a blunt rod and directing the rod and ribbon to the predetermined area of the fascia or skeletal structure.

9. A method of repairing ptosis of the breast and other defects of a mammary gland, comprising:
attaching a ribbon of physiologically inert mesh to the inferior border of the underside of the mammary gland;
conducting each end of the ribbon beneath the surface of the skin upward to a predetermined area of the fascia or the skeletal structure above the mammary, and;
attaching each end of the ribbon to the skeletal structure or fascia above the mammary, the ribbon being sufficiently taut to impede the fall of the breast below a predetermined position.

10. The method of claim 9, wherein the conduction of the ribbon beneath the surface of the skin is accomplished by attaching either end of the ribbon to a blunt rod and directing the rod and ribbon to the predetermined area of the fascia or skeletal structure.

* * * * *